United States Patent [19]

Sano et al.

[11] Patent Number: 4,778,808
[45] Date of Patent: Oct. 18, 1988

[54] FEED ADDITIVE CONTAINING TRYPTOPHAN

[75] Inventors: Chiaki Sano, Tokyo; Yoshimi Nagano, Kawasaki; Kiyoshi Tanaka, Tokyo; Shigeho Ikeda; Masayoshi Naruse, both of Yokohama, all of Japan

[73] Assignee: Ajinomoto Co., Inc., Tokyo, Japan

[21] Appl. No.: 839,041

[22] Filed: Mar. 12, 1986

[30] Foreign Application Priority Data

Mar. 15, 1985 [JP] Japan .................. 60-52862

[51] Int. Cl.$^4$ .................. C07D 209/20; A61K 31/405
[52] U.S. Cl. .................................. 514/419; 548/497; 426/2
[58] Field of Search .................. 548/497; 514/419

[56] References Cited

FOREIGN PATENT DOCUMENTS

| 4010146 | 5/1965 | Japan | 548/497 |
| 42-15541 | of 1967 | Japan . | |
| 0013758 | 1/1985 | Japan | 548/497 |
| 2172888 | 5/1986 | United Kingdom | 548/497 |

Primary Examiner—Richard L. Raymond
Assistant Examiner—D. B. Springer
Attorney, Agent, or Firm—Oblon, Fisher, Spivak, McClelland & Maier

[57] ABSTRACT

A feed additive produced by concentrating an aqueous solution containing tryptophan and impurities both originating in the culture broth of a tryptophan-producing microorganism, with the pH of the aqueous solution being maintained in the range of 4 to 6 and the temperature thereof being maintained in the range of 20° to 80° C. during the process of concentrating.

10 Claims, 1 Drawing Sheet

FEED ADDITIVE CONTAINING TRYPTOPHAN

BACKGROUND OF THE INVENTION

1. Field of the Invention

This invention relates to a novel composition usable as an animal feed additive.

2. Description of the Background

Tryptophan is one of the essential amino acids for animals and can be produced by either a chemical process or a biochemical process. One typical biochemical process is known to produce tryptophan by culturing a tryptophan-producing microorganism in a medium using saccharides as principal carbon sources and ammonia or other nitrogen-containing substances as principal nitrogen sources. The tryptophan consequently produced in the culture broth is isolated from the culture broth, purified, and then put to use in animal feed. Successful use in animal feed of the tryptophan as contained in the culture broth not specifically isolated from the impurities inherent in the culture broth or otherwise purified has never been reported in the literature.

Furthermore, tryptophan is highly susceptible to chemical changes such as decomposition. It is known that when a fermentation broth containing the produced tryptophan is concentrated and dehydrated by ordinary procedures described in the literature, the tryptophan in the fermentation broth will be colored and will be substantially lost through hydrolysis.

SUMMARY OF THE INVENTION

Accordingly, it is an object of this invention to produce from a culture broth of tryptophan, a composition free from substances detrimental to animals, stable, and not inferior in nutritional effect to the isolated tryptophan without requiring any special process of purification or entailing any hydrolysis of tryptophan.

This and other objects of the invention as will hereinafter become more readily apparent have been accomplished by providing a feed additive produced by the process of concentrating an aqueous solution containing tryptophan and impurities both originating in a culture broth of a tryptophan-producing microorganism while maintaining the pH of the aqueous solution in the range of from 4 to 6 and the temperature thereof in the range of from 20° C. to 80° C.

BRIEF DESCRIPTION OF THE DRAWINGS

The FIGURE generally represents the results of the test in Example 2 in which pH was adjusted during a heating process and the effect of tryptophan was measured.

DETAILED DESCRIPTION OF THE PREFERRED EMBODIMENTS

Figure 1:
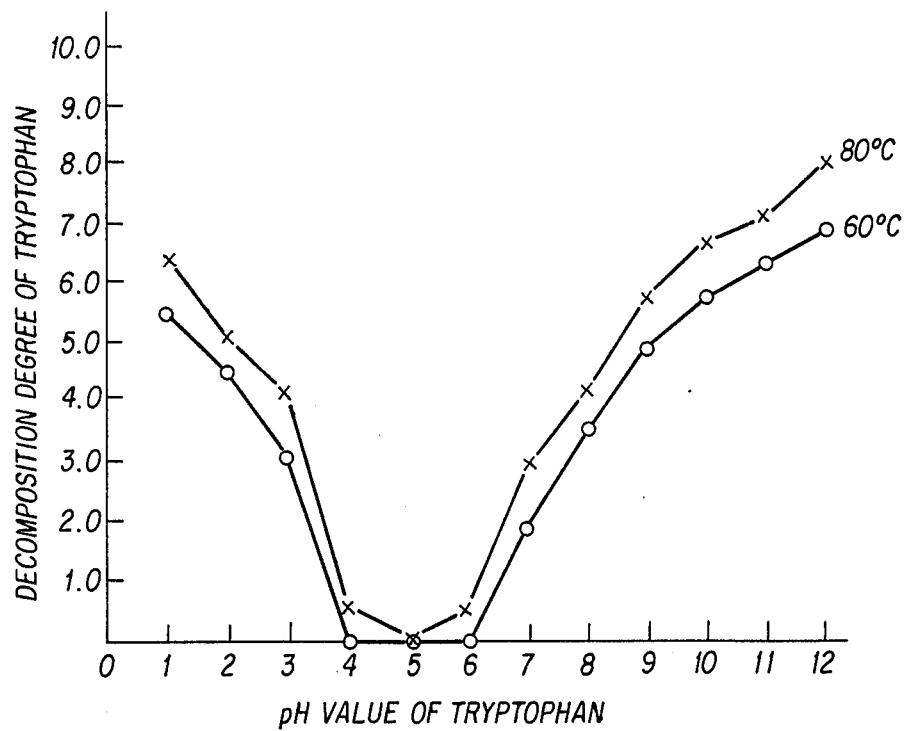

The present inventors have found that a composition produced by concentrating an aqueous solution containing tryptophan (tryptophan content: 10 to 70%, preferably 20 to 50%, based on the total solids content at the beginning of the concentration process) and impurities both originating in the culture broth of a tryptophan-producing microorganism, while keeping the pH of the aqueous solution in the range of 4 to 6, preferably 4.5 to 5.5, and the temperature thereof in the range of 20° to 80° C., preferably 40° to 80° C., and optionally drying the concentrate (at a temperature in the range of 60° to 120° C.), possesses the same nutritional effect as pure tryptophan. The process prevents tryptophan from undergoing hydrolysis or forming colored matter. The impurities originating in the culture broth offer no hindrance to the use of the composition in an animal feed when the composition is prepared in this manner, and the composition shows sufficient stability to warrant a long shelf life. The present invention has been perfected on the basis of this discovery.

Any microorganism can be effectively used in this invention on the sole condition that it should possess an ability to produce tryptophan. Specific examples of microorganisms include types deposited under PERM-P 6258, PERM-P 5236, ATCC-21427, FERM-P 6026, and FERM-P 6027. Additional examples are set forth in the following table:

| Microorganisms | NRRL | FERM BP | ATCC | FERM P |
|---|---|---|---|---|
| Brevibacterium flavum | — | — | 21427 | |
| Brevibacterium flavum | (NRRL 841211) | — | | |
| Flavobacterium autothermophilium | | — | | FERM P-4425 |
| Arthrobacter globiformis | | — | | FERM P-5296 |
| Microbacterium ammoniaphilum | | — | | FERM P-5298 |
| Escherichia coli | | — | | FERM P-5300 |
| Brevibacterium flavum | | FERM BP-114 | | |
| Bacillus subtilis | | FERM BP-208 | | |
| Bacillus subtilis | | FERM BP-209 | | |
| Brevibacterium flavum | | FERM BP-475 | | |
| Corynebacterium glutamicum | | FERM BP-478 | | |
| Bacillus subtilis | | FERM BP-202 | | |
| Brevibacterium lactofermentum | | — | | FERM P-7126 |

The culture of the tryptophan-producing microorganism can be carried out without entailing any special difficulty by any of the conventional methods such as are disclosed in the specification of Japanese patent application Laid-open SHO No. 58(1983)-107,190, SHO No. 58(1983)-138,389, and SHO No. 57(1982)-208,994.

The starting material for the production of the composition of this invention can be the culture broth in its unmodified form. Optionally, the culture broth may undergo a primary refining treatment, such as separation of used microorganic cells or decolorization of the broth with activated carbon or an ion-exchange resin (such as, for example, a nonpolar macroporous resin produced by Mitsubishi Chemical Industry and marketed under trademark designation of "DIAION SP-207"). The culture broth in whatever form can be adopted as the starting material on the sole condition that the tryptophan content thereof should fall in the range of 10 to 70% based on the total solids content thereof.

Any carbon source which is assimilable by the tryptophan-producing microorganism can be used as a carbon source in the culture medium. Use of a raw material having a highly assimilable carbon-source content is desirable as this decreases the amount of the residue remaining after the completion of the fermentation process. Thus, the loss of tryptophan due to the reaction of tryptophan with the residue consequently decreases in proportion as the assimilability of the carbon source content increases. Concrete examples of the raw material of such highly assimilable carbon source content include crystalline glucose and sucrose and saccharified starch solution.

For adjustment of the pH of the tryptophan culture broth, any ordinary mineral acid or organic acid which contains no substance detrimental to animals can be used. Nitrous acid and aldehyde-containing organic acids are not usable for the pH adjustment because they readily react with tryptophan.

Concentrating is continued until the solids content of the solution falls within the range of 50 to 70%, preferably about 60%, after which the additional drying steps described herein can be carried out.

During the courses of concentration and dehydration, the aqueous solution being concentrated and the concentrate being dehydrated can be kept under a vacuum for the purpose of lowering the boiling point of water in the system under treatment. Addition to the fermentation broth of a substance not harmful to the animals and capable fo forming an azeotropic mixture with water, thereby lowering the boiling point of water, proves advantageous because the added substance is effective in lowering the temperature of the solution under treatment, preventing tryptophan from hydrolysis and coloration and, at the same time, enhancing the fluidity of the solution and permitting use of a multipurpose reactor vessel up to a high level of concentration. Thus, the addition of the azeotropic substance is advantageous from the standpoint of energy saving.

The tryptophan composition obtained as described above possesses an equal nutritional value for animals to refined tryptophan.

The product of this invention can be produced inexpensively by a simple procedure from a fermentation broth containing tryptophan without requiring isolation and purification of tryptophan or entailing hydrolysis of tryptophan or formation of colored matter. It permits the greatest possible utility of tryptophan nutritionally.

Now the present invention will be described more specifically below with reference to working examples.

EXAMPLE 1

Eight liters of a tryptophan culture medium of the composition shown in the following table were placed in a jar fermenter having an inner volume of 20 liters and sterilized. An inoculum of FERM-P 6258 disclosed in the specification of Japanese patent application Laid-open SHO No. 58(1983)-107,190 was cultured on the culture medium, with the solution aerated at ½ VVm, stirred at 350 rpm, kept at 31.5° C., and adjusted to pH 7.0 with aqueous ammonia. Halfway along the entire course of culturing, continuous feeding of the glucose solution was started. Consequently, there were obtained 10 liters of a fermented both containing 2 g of tryptophan per dl with a total solids content of 6.7 g/dl.

| Composition of tryptophan culture medium | |
|---|---|
| Glucose | 13 g/dl |
| NH$_4$Cl | 1 g/dl |
| KH$_2$PO$_4$ | 0.1 g/dl |
| KCl | 0.2 g/dl |
| MnSO$_4$.7H$_2$O | 0.001 g/dl |
| FeSO$_4$.4H$_2$O | 0.001 g/dl |
| MgSO$_4$.7H$_2$O | 0.04 g/dl |
| HCl hydrolyzate of soybean protein | 0.1 g/dl (as total nitrogen) |
| Soybean oil as | 0.01 ml/dl |

| -continued | |
|---|---|
| Composition of tryptophan culture medium | |
| defoaming agent | |

(Concentration and dehydration)

The fermented broth, 10 liters, obtained by the procedure described above was adjusted to pH 4.5 with sulfuric acid (60%) and, by the use of a Ruhr vacuum-concentration device, concentrated under a vacuum at a temperature not exceeding 60° C. until the solids content thereof reached about 60% by weight.

The resulting concentrate was dried with a continuous vacuum belt drier until the water content thereof fell below 1%. During the course of this drying, while the water content was above 5%, the vapor pressure and the degree of vacuum were adjusted so as to prevent the temperature of the solution from rising above 80° C.

The tryptophan powder consequently produced had the same tryptophan content based on the total solids content as that of the fermented broth based on its total solids content. This tryptophan powder showed no discernible increase in color over the fermented broth.

The tryptophan powder possessed very low hygroscopicity, showing an equilibrium water content of not more than 16% under the conditions of 40° C. and 70% relative humidity.

The tryptophan content based on the total solids content was also equal to the tryptophan content of the pH-adjusted fermentation broth based on the total solids content. The tryptophan powder likewise showed no discernible increase in color over the fermentation broth.

EXAMPLE 2

(pH condition and hydrolysis ratio of tryptophan fermented broth)

Aliquots of the same concentrate of fermented broth (solids content about 60% by weight) as obtained in Example 1 were adjusted to varying pH levels between pH 1 and pH 12 with hydrochloric acid and sodium hydroxide and then diluted with water to a fixed tryptophan concentration of 2 g/dl.

The samples so produced were severally placed in screw containers having an inner volume of 100 ml and heated in an oil bath kept at 60° C. or 80° C. for six hours. The hot samples were suddenly cooled and analyzed for tryptophan concentration.

The results are shown in the FIGURE. It is noted from the graph that the hydrolysis of tryptophan was notably curbed by adjusting the pH of the sample during concentration to be in the range of 4 to 6.

EXAMPLE 3

(feed test)

A basic feed having a crude protein content of 12% was prepared by combining a mixture of 87.0% of Indian corn and 9.5% of defatted soybean, a mixture of such minerals as calcium phosphate and sodium chloride with vitamins, and amino acids, i.e., 0.3% of L-LysHCl, 0.1% of DL-methionine, and 0.1% of L-threonine. The basic feed plus a given sample equivalent to 0.04% of L-tryptophan was fed to fully grown pigs to test for nutritional effect of the added sample. The results of the test were as shown below.

|  | Test group | | |
| --- | --- | --- | --- |
| Sample | 1<br>No tryptophan | 2<br>Pure L-tryptophan | 3<br>Product of this invention (0.04% as L-tryptophan) |
| Increase of body weight per day (g) | 480 | 620 | 621 |
| Amount of feed consumed per day | 1.35 | 1.50 | 1.50 |
| Feed demand ratio | 2.76 | 2.42 | 2.42 |

(Method of test) Each test batch consisting of 8 (4 castrated male and 4 female) fully grown pigs were fed on the basic feed plus the designated sample for 28 days (between the body weight levels of 18 kg and 35 kg), to determine changes in average body weight.
(Results) The product of this invention showed the same effect in increasing body weight per day and enhancing feed demand ratio as pure tryptophan.

EXAMPLE 4

The L-tryptophan producer used was a mutant derived from *Corynebacterium glutamicum* (FERM P-7374). A mutant was disclosed in the specification of Japanese patent application Laid-open SHO No. 60(1985)-137,298. This mutant identified above by FERM P number was originally deposited on Dec. 19, 1983, at the Fermemntation Research Institute, Agency of Industrial Sciences and Technology, Ministry of International Trade and Industry (FRI), 1-3, Higashi 1-chome, Yatabemachi, Tsukuba-gun, Ibaragi-ken 305, Japan, and was accorded the FERM-P number indicated above. The mutant deposited was then converted into deposit under Budapest Treaty on Feb. 2, 1984, and was accorded the corresponding FERM BP-478.

In order to perform fermentation with a working volume of 10 liter, the medium components shown in the following table were dissolved with 8 liters tap water in a 20-liter jar fermenter. The medium was sterilized at 120° C. for 20 min by introducing high-pressure steam.

| Composition of tryptophan culture medium | |
| --- | --- |
| Molasses | 100 g/l<br>(conversion based on glucose) |
| $KH_2PO_4$ | 0.5 g/l |
| $K_2HPO_4$ | 0.25 g/l |
| $MgSO_4.7H_2O$ | 0.25 g/l |
| $(NH_4)_2SO_4$ | 20 g/l |
| Corn steep liquor | 10 g/l |
| L-Phenylalanine | 200 mg/l |
| L-tyrosine | 175 mg/l |
| pH 7.2 | |

The jar fermentor was inoculated with the seeding culture at a ratio of 5%, which was obtained by growing the cells in a liquid medium. Fermentation was carried out at 31.5° C. The pH of the medium was maintained at 6.5 with gaseous ammonia, agitation speed was 350 rm and the air flow rate was ½ vvm. In the courese of fermentation, glucose was continuously added to the jar fermentor.

Glucose was almost completely consumed, and 1.8 g/dl L-tryptophan was accumulated in the cultured broth of 10 liters with a total solids content of 6.0 g/dl.

The fermented broth, 10 liters, obtained by the procedure described above, was adjusted to pH 4.5 with sulfuric acid (60%) and, by the use of a Ruhr vacuum-concentration device, concentrated under a vacuum at a temperature not exceeding 60° C. as a material temperature until the solids content thereof reached about 60% by weight.

The resultant concentrate was dried with heated air at 115° C. using a spray drier at a temperature not exceeding 100° C. as the material temperature. The water content of the dried matter thus obtained was 2.0%.

The tryptophan powder consequently produced had the same tryptophan content based on the total-solids content as that of the fermented broth based on its total solids content. This tryptophan powder showed no discernible increase in color over the fermented broth.

EXAMPLE 5

Eight liters of a tryptophan culture medium of the composition shown in the following table was placed in a jar fermenter having an inner volume of 20 liters, and sterilized, and an inoculum of FERM P-5907 disclosed in the specification of Japanese patent application Laid-open SHO No. 57(1982)-174,096, *Brevibacterium flavum* FERM BP-114 deposited under the rules of The Budapest Treaty, was cultured on the culture medium, with the solution aerated at 178 VVm, stirred at 350 rpm, kept at 31.5° C., and adjusted to pH 7.0 with aqueous ammonia. Halfway along the entire course of culturing, continuous feeding of the glucose solution was started. Consequently, there was obtained 10 liters of a fermented broth containing 1.4 g of tryptophan per dl with a total solids content of 5.6 g/dl.

| Composition of tryptophan culture medium | |
| --- | --- |
| Glucose | 130 g/l |
| $(NH_4)_2SO_4$ | 25 g/l |
| $KH_2PO_4$ | 1 g/l |
| fumaric acid | 12 g/l |
| acetic acid | 3 ml/l |
| $MnSO_4.7H_2O$ | 8 mg/l |
| d-biotin | 50 μg/l |
| Vitamine Bi—HCl | 2000 μg/l |
| L-tyrosine | 650 mg/l |
| DL-methionine | 400 mg/l |
| Soybean protein acid hydrolysate solution | 50 ml/l |
| $MgSO_4.7H_2O$ | 1 g/l |
| pH 6.5 | |

The fermented broth, 10 liters, obtained by the procedure described above was adjusted to pH 4.5 with sulfuric acid (60%) and, by the use of a Ruhr vacuum-concentration device, concentrated under a vacuum at a temperature not exceeding 60° C. as the material temperature until the solids content thereof reached about 60% by weight.

The resultant concentrate was dried with heated air at 115° C. using a spray-drier at a temperature not exceeding 100° C. as a material temperature. The water content of the dried matter thus obtained was 2.0%.

The tryptophan powder consequently produced had the same tryptophan content based on the total solids content as that of the fermented broth based on its total solids content. This tryptophan powder showed no discernible increase in color over the fermented broth.

The invention now being fully disclosed, it will be apparent to those of ordinary skill in the art that many changes and modifications can be made thereto without departing from the spirit or scope of the invention as set forth herein.

What is claimed as new and desired to be secured by Letters Patent of the United States is:

1. A feed additive containing tryptophan, which is produced by a process which comprises:

concentrating an aqueous solution containing tryptophan and impurities obtained by culturing a tryptophan-producing microorganism in a culture broth while maintaining the pH of the aqueous solution in the range of 4 to 6 and the temperature in the range of 20° to 80° C., and wherein the content of tryptophan in said aqueous solution is in the range of from 10 to 70% based on the total solids content of said aqueous solution.

2. The feed additive of claim 1, wherein the tryptophan content is in the range of from 20 to 50% based on the total solids content.

3. The feed additive of claim 1, wherein the pH of said aqueous solution during the course of said concentrating is in the range of 4.5 to 5.5.

4. The feed additive of claim 1, wherein the temperature of said aqueous solution during the course of said concentrating is in the range of from 40° to 80° C.

5. The feed additive of claim 1, wherein a concentrate obtained by said concentrating is subsequently dried at a temperature in the range of from 60° to 120° C.

6. A method for producing a tryptophan-containing feed additive, which comprises:

concentrating an aqueous solution containing tryptophan and impurities obtained by culturing the tryptophan-producing microorganism in a culture broth while maintaining the pH of said aqeous solution in the range of 4 to 6 and the temperature of said aqueous solution in the range of 20° to 80° C., and wherein the content of tryptophan in said aqueous solution is in the range of from 10 to 70% based on the total solids content of said aqueous solution.

7. The method of claim 6, wherein the tryptophan content is in the range of from 20 to 50% by weight based on the total solids content.

8. The method of claim 6, wherein the pH of said aqueous solution during said concentrating is in the range of from 4.5 to 5.5.

9. The method of claim 6, wherein the temperature of said aqueous solution during said concentrating is in the range of from 40° to 80° C.

10. The method of claim 6, wherein a concentrate produced by said concentrating is subsequently dried at a temperature in the range of from 60° to 120° C.

* * * * *

UNITED STATES PATENT AND TRADEMARK OFFICE
CERTIFICATE OF CORRECTION

PATENT NO.   :   4,778,808
DATED        :   OCTOBER 18, 1988
INVENTOR(S)  :   CHIAKI SANO ET AL

It is certified that error appears in the above-identified patent and that said Letters Patent is hereby corrected as shown below:

Column 1, line 43, delete "both" and insert --broth--;

line 49, delete "generally" and insert --graphically--.

Column 2, line 21, delete "autothermophilium" and insert --autothermophilum--;

line 63, delete "carbon-source" and insert --carbon source--.

Column 3, line 21, delete "fo" and insert --of--;

line 55, delete "both" and insert --broth--.

Column 5, line 26, delete "Fermemntation" and insert --Fermentation--;

line 30, delete "Yatabemachi" and insert --Yatabe-machi--;

line 36, delete "liter" and insert --liters--;

line 53, delete "fermentor" and insert --fermenter--;

line 58, delete "air flow" and insert --airflow--;

UNITED STATES PATENT AND TRADEMARK OFFICE
CERTIFICATE OF CORRECTION

PATENT NO. : 4,778,808
DATED : OCTOBER 18, 1988
INVENTOR(S) : CHIAKI SANO ET AL

It is certified that error appears in the above-identified patent and that said Letters Patent is hereby corrected as shown below:

line 58, delete "vvm" and insert --VVM--;

line 58, delete "courese" and insert --course--;

line 60, delete "fermentor" and insert --fermenter--.

Column 6, line 8, delete "total-solids" and insert --total solids--;

line 38, delete "Vitamine" and insert --Vitamin--;

line 54, delete "spray-drier" and insert --spray dryer--.

Column 8, line 6, delete "aqeous" and insert --aqueous--.

Signed and Sealed this

Twenty-seventh Day of February, 1990

Attest:

JEFFREY M. SAMUELS

*Attesting Officer*     *Acting Commissioner of Patents and Trademarks*